United States Patent [19]
deCoriolis et al.

[11] Patent Number: 5,342,408
[45] Date of Patent: Aug. 30, 1994

[54] TELEMETRY SYSTEM FOR AN IMPLANTABLE CARDIAC DEVICE

[75] Inventors: Paul E. deCoriolis, Bellevue; Craig S. Siegman, Redmond; Joseph M. Bocek, Seattle, all of Wash.

[73] Assignee: InControl, Inc., Redmond, Wash.

[21] Appl. No.: 1,330

[22] Filed: Jan. 7, 1993

[51] Int. Cl.⁵ .............................................. A61N 1/362
[52] U.S. Cl. ....................................................... 607/32
[58] Field of Search ............... 607/30, 31, 32, 27, 607/17

[56] References Cited

U.S. PATENT DOCUMENTS

| | | | |
|---|---|---|---|
| 4,026,305 | 5/1977 | Brownlee et al. | 607/17 |
| 4,223,679 | 9/1980 | Schulman et al. | 607/9 |
| 4,281,664 | 8/1981 | Duggan | 128/696 |
| 4,361,153 | 11/1982 | Slocum et al. | 607/5 |
| 4,416,283 | 11/1983 | Slocum | 607/5 |
| 4,432,360 | 2/1984 | Mumford et al. | 607/5 |
| 4,453,162 | 6/1984 | Money et al. | 128/903 |
| 4,494,545 | 1/1985 | Slocum et al. | 607/27 |
| 4,519,401 | 5/1985 | Ko et al. | 128/748 |
| 4,541,431 | 9/1985 | Ibrahim et al. | 607/27 |
| 4,543,953 | 10/1985 | Slocum et al. | 607/27 |
| 4,550,732 | 11/1985 | Batty, Jr. et al. | 607/27 |
| 4,556,063 | 12/1985 | Thompson et al. | 607/27 |
| 4,561,442 | 12/1985 | Vollmann et al. | 607/27 |
| 4,562,840 | 1/1986 | Batina et al. | 607/32 |
| 4,571,589 | 2/1986 | Slocum et al. | 128/631 |
| 4,681,111 | 7/1987 | Silvian | 607/59 |
| 4,741,340 | 5/1988 | Batina et al. | 607/27 |
| 4,757,816 | 7/1988 | Ryan et al. | 607/32 |
| 4,809,697 | 3/1989 | Causey, III et al. | 607/31 |
| 4,847,617 | 7/1989 | Silvian | 607/27 |
| 4,875,483 | 10/1989 | Vollmann et al. | 607/15 |
| 4,944,299 | 7/1990 | Silvian | 607/32 |
| 5,081,987 | 1/1992 | Nigam | 607/32 |

*Primary Examiner*—Kyle L. Howell
*Assistant Examiner*—George Manuel
*Attorney, Agent, or Firm*—Foley & Lardner

[57] ABSTRACT

A telemetry system and method of monitoring cardiac activity or providing therapy to the heart for an implantable cardiac device. The system includes a receiver and a transmitter in an external programmer and a receiver section and transmitter section in the cardiac device. The receiver section and the transmitter section of the cardiac device generally remain in a de-energized state. The receiver section is energized at spaced apart time intervals to detect an initiation signal transmitted by the external programmer. If the initiation signal is detected, the receiver section and the transmitter section of the cardiac device are fully activated. The external programmer includes a signal strength indicating means for providing an indication of received signal strength which the user can use to position the receiver and transmitter in the external programmer for optimum received signal strength. An antenna is disposed in the header of the implanted device to facilitate communication at high speed.

63 Claims, 5 Drawing Sheets

TELEMETRY SYSTEM FOR AN IMPLANTABLE CARDIAC DEVICE

BACKGROUND OF THE INVENTION

The present invention generally relates to a telemetry system for an implantable cardiac device. The present invention is more particularly directed to a telemetry system for an implantable cardiac device which monitors activity of a human heart, which also may additionally deliver therapy to the human heart, and which communicates with a non-implanted external device. The present invention is more particularly directed to a cardiac device which utilizes such a system to provide reduced power consumption while communicating data and command transmissions at a high transmission rate and with error correction and detection to assure accurate transmission even in noisy environments.

Implantable cardiac devices are designed to be small in size and implanted beneath the skin of a patient. Such devices establish electrical contact with the heart by one or more electrical leads having electrodes implanted within the heart, attached to the surface of the heart, or disposed subcutaneously and spaced from the heart.

Implantable cardiac devices include devices which monitor heart activity. Monitoring heart activity includes sensing electrical signals generated by the heart, recording data indicative of the sensed electrical signals and analyzing the recorded data to provide characterization data of the heart activity. Such devices detect arrhythmias of the heart, ischemia, or other conditions. The implantable device, under direction of a microprocessor, generates data indicative of these conditions and stores the data in memory. The data may be retrieved by an external device through telemetry.

In addition to monitoring heart activity, cardiac devices may also provide corrective therapy to the heart in the form of applied electrical energy. One such cardiac device is an implantable atrial defibrillator. Atrial defibrillators function to sense heart activity and deliver cardioverting or defibrillating electrical energy to the atria of the heart when the atria are in need of cardioversion. Control of these devices is provided by internal circuit means including devices such as a microprocessor. The microprocessor may be coupled to sensing means which sense the electrical activity of the heart and produce digital data corresponding to the sensed electrical activity. An atrial defibrillator implemented in the microprocessor in turn analyzes the digital data to detect conditions such as fibrillation of the atria. In response to detecting such a condition, the microprocessor directs other circuitry to apply defibrillating electrical energy to the atria of the heart to defibrillate the atria and return the heart to a normal rhythm.

Implanted cardiac devices such as these may receive command instructions from a non-implanted device such as a programmer which is external to the skin of the patient. These command instructions are referred herein as inbound transmissions, viewed from the perspective of the implanted device. The received command instructions may include program instructions or steps for directing the microprocessor's operation. The received command instructions may also include data such as program limits and timing data.

Similarly, the implantable cardiac device may transmit ECG or characterization data and other information to the external device. These are referred to herein as outbound transmissions, viewed from the perspective of the implanted device. The programmer may function to receive information from the implanted device as well as to transmit command transmissions including programming commands to the implanted device. Communication between the implanted device and the programmer may be limited to transmissions by only one of the devices with the other device receiving those transmissions. Alternatively, communication between the implanted device and the programmer may include transmissions by both devices.

Such communication is facilitated by receiving and transmitting means included in the implantable cardiac device and in the programmer. Where the implantable cardiac device includes a microprocessor, the receiving and transmitting means may cooperate with the microprocessor to receive command transmissions from the programmer and to transmit data and other information to the programmer. The programmer includes analogous transmitting and receiving means for communicating with the implanted cardiac device. Both the implanted cardiac device and the programmer include antenna means coupled to the receiving and transmitting means for transmitting and receiving electromagnetic energy.

Prior art devices typically enclose the antenna or antennas of the implanted cardiac device inside the enclosure of the implanted device. Such enclosures are typically metallic in nature and may be made of titanium. Metal enclosures act as low pass filters to limit the bandwidth of signals transmitted from and received by the implanted cardiac devices. Prior art designs which enclosed the antennas in the enclosure have experienced limited data transmission rates of less than 10K bits/second.

In prior art designs, bandwidth is also kept low in order to minimize the power consumed by the implanted cardiac device. Power consumption is a very important criterion in designing implantable devices. Such devices are typically powered by a depletable energy source such as a battery. A depleted energy source requires replacement of the cardiac device which can be costly and inconvenient and with potential risk to the patient. Accordingly, there is a need for an implanted cardiac device which exhibits minimized power consumption.

In accordance with the present invention, power consumption is minimized by de-energizing circuit components which are not currently required to be activated. Where the digital logic portions of an implantable cardiac device are fabricated in CMOS (complementary metal-oxide-semiconductor), this deactivation is inherent. Digital CMOS devices consume power only when switching, as is well known. Some portions of the circuitry of an implanted cardiac device are analog rather than digital in operation or are not fabricated in CMOS. Examples of this are the receiving means of the implanted device.

Both the receiving means and the transmitting means of an implanted cardiac device are used only intermittently to communicate with the programmer. After command transmissions are received from the programmer or after data and other information is transmitted to the programmer, the receiving means and transmitting means may remain inactive for extended periods of time. Accordingly, these circuits are well-suited to being de-energized when not in use in order to minimize power consumption.

However, when transmitting means and receiving means are de-energized to reduce power consumption, a further problem is created in that the implanted cardiac device is unable to receive command transmissions when its receiver is de-energized. Therefore, there is a need for activation means for activating the de-energized portions of the implanted cardiac device to allow the implanted device to receive command transmissions from the programmer.

One possible design for activating the device is passive wakeup. According to such a design, the programmer transmits a wakeup command with sufficient energy to convert the receiving means of the implanted device from a quiescent state, in which receiving and transmitting circuits are de-energized, to an active state, in which the implanted device and programmer are communicating. However, a relatively large receiving antenna is required in order to couple sufficient electromagnetic energy to the receiving means to facilitate this wakeup function. Such an antenna may be inconsistent with a physically compact implanted cardiac device or with an implanted cardiac device with the antenna in the header. The header is the epoxy or other non-metallic cover which sealingly engages the metallic enclosure of the implantable cardiac device. Some prior art devices use a large, flat antenna within the hermetic can. Even in a compact device, the antenna may be large enough that a wakeup command can be received by a quiescent circuit. However, once the antenna is made small enough to fit in the header, the need for an active circuit to receive the wakeup command becomes apparent. Therefore, there is a need for an implanted device having receiving means which may rest in a quiescent state and requires only a single, relatively small antenna while still providing reduced power consumption.

The present invention provides such a telemetry system. In accordance with the present invention, active wakeup is employed for activating de-energized portions of the implantable cardiac device. In accordance with this embodiment, the receiving means generally remains in a de-energized, quiescent state. At spaced apart time intervals, the receiving means is converted to an active state for a predetermined and relatively short time period in which it is energized and capable of sensing energy transmitted by the programmer. If no energy is sensed, the receiving means returns to the quiescent state. If energy is sensed, and the correct code is received, the transmitting means is energized to transmit a response code to the programmer. The response code indicates to the programmer that the implanted cardiac device is active and able to communicate. Accordingly, a single, relatively small antenna may be employed for both transmitting and receiving.

Such active wakeup in accordance with the present invention further allows for transmission of command transmissions at more than one data rate. Transmission of command transmissions at a low data rate allows the circuitry in the implanted cardiac device to operate at a low clock rate. As is well known, power consumption of CMOS digital logic devices is proportional to the clock rate of those devices. A low clock rate permits reduced power consumption. In accordance with the present invention, a low clock rate is used when the receiving means and transmitting means are in a quiescent state or when the receiving means is sensing energy from the programmer. Once the response code has been sent to the programmer and a communications link has been established, the low clock rate is converted to a high clock rate. Command transmissions are then transmitted at a high data rate consistent with the high clock rate of the implanted cardiac device. Transmission of data at a high data rate provides the further advantage of reducing power consumption by reducing the duration of time periods during which the receiving means and transmitting means must be in the active state.

In addition to power reduction, another important design criterion for implanted cardiac devices is accurate communication of data. Command transmissions transmitted from the programmer to the implanted cardiac device must be received correctly. Similarly, information including data transmitted by the implanted device must be received correctly. This communication must occur in environments such as hospitals and doctors' offices which may be very noisy due to the presence of other electronic equipment and other electromagnetic sources.

Therefore, there is a need for a telemetry system for implantable cardiac devices capable of transmitting and receiving data in noisy environments. Moreover, there is a need for such a telemetry system with the capability of detecting errors in data transmission and correcting those errors.

The present invention provides such a telemetry system. An implantable cardiac device in accordance with the present invention communicates with the programmer according to a communications protocol. Preferably, inbound transmissions are transmitted in accordance with a first protocol, and outbound transmissions are transmitted in accordance with a second protocol. According to both the first and second protocols, data is transmitted in packets. Each packet includes one or more frames. Moreover, each frame contains error detection codes used to detect bit-level errors. Each frame includes identifying information. In the event of such errors, only the frame or frames containing the errors need be re-transmitted (for the second protocol only). Thus, the ability to detect and correct errors without requiring the re-transmission of an entire transmission further reduces power consumption in such a telemetry system.

A further aspect of assuring accuracy of transmitted data is establishing a reliable data link. Generally, programmer antennas are disposed in moveable programmer heads which are to be placed in close proximity to the implantation site of the cardiac device. Because the implanted cardiac device is implanted and not visible, determining the proper orientation of the programming head of the external device can be difficult. To assure that data is transmitted accurately, the programming head antennas must be positioned to maximize signal strength received from the implanted cardiac device. Accordingly, there is a need for a telemetry system which provides an indication to the user of the relative received signal strength so that the antennas of the programming head can be positioned properly.

The present invention provides such a telemetry system. The telemetry system in accordance with the present invention includes a signal strength indicating means in the movable programming unit coupled to the programmer. The movable programming unit can be positioned external to the skin of the patient. An indication of received signal strength is provided to allow repositioning of the movable programming unit to maximize received signal strength.

In addition to assuring reliable communication of command transmissions and response information, another important design criterion for implantable cardiac devices is the ability to avoid locked-up devices after final manufacture of the device. The possibility exists that an implantable cardiac device may become completely inert after the final manufacturing step of welding the enclosure of the cardiac device. That is, the cardiac device may generate no output and not respond to telemetry transmissions. Accordingly, there is a need for a telemetry system including a hardware reset operation which will reset the cardiac device to a predetermined initial state. For this operation to function properly, the receiving means and transmitting means of the cardiac device must be able to operate independently of the microprocessor. The present invention provides such a telemetry system.

SUMMARY OF THE INVENTION

The present invention therefore provides a cardiac device which monitors activity of a human heart or provides therapy to the heart or both. The device is implantable beneath the skin of a patient and includes at least one electrode for sensing activity of the heart and circuit means for monitoring the activity sensed by the at least one electrode and for generating data indicative of that activity in accordance with received command transmissions. The cardiac device further includes telemetry means for communicating with a non-implanted external receiver and transmitter. The telemetry means includes receiving means for receiving the command transmissions which conform to a first protocol. The telemetry means further includes transmitting means for transmitting information including data to the non-implanted external receiver. The transmission of the information conforms to a second protocol which is different from the first protocol.

The present invention further provides a cardiac device which monitors activity of or provides therapy to a human heart or both. The cardiac device is implantable beneath the skin of a patient and includes at least one electrode for sensing activity of the heart and circuit means for monitoring the activity sensed by the at least one electrode in accordance with received command transmissions transmitted from a non-implanted transmitter external to the skin of the patient. The cardiac device further includes receiving means for receiving the command transmissions and activation means for enabling the receiving means at intervals in time of controlled duration, separated by intervals in time during which reception does not occur.

The cardiac device may further include transmitting means for transmitting information including data indicative of monitored activity to a non-implanted receiver. The receiving means may further include a receive amplifier.

The activation means may enable the receive amplifier to detect a transmission command from the non-implanted transmitter during a predetermined time period during each interval of the intervals in time of controlled duration. In response to the receive amplifier detecting the transmission command, the activation means may enable the transmitter which transmits a response code to the non-implanted receiver. Both the receiving means and the transmitting means may be de-energized when disabled.

The cardiac device may further include reset means for initializing the cardiac device to a predetermined state. The reset means may operate independently of the circuit means and may be responsive to a reset command transmitted from the non-implanted transmitter.

The present invention still further provides a cardiac monitoring system for monitoring activity of or providing therapy to a human heart of a patient. The system includes a cardiac device fully implantable beneath the skin of the patient for monitoring activity of the heart in accordance with received program command transmissions transmitted from external to the skin of the patient. The system further includes telemetry means including receiving means within the cardiac device for receiving the program command transmissions, transmitting means within the cardiac device for transmitting information including locating signals, and a movable programing unit including external transmitting means for transmitting the program command transmissions, external receiving means for receiving the information and signal strength indicating means for indicating a received strength of said locating signals.

The present invention still further provides a method of communicating in a cardiac monitoring and/or therapeutic device. The method includes the steps of sensing activity of the heart, generating data indicative of the activity in accordance with received command transmissions, providing a receiver and receiving from a non-implanted transmitter the command transmissions conforming to a first protocol at two or more rates, and transmitting information including the data to a non-implanted receiver in accordance with a second protocol at one or more rates, the second protocol being different from the first protocol.

The present invention still further provides a method of communicating in a cardiac monitoring or therapeutic device. The method includes the steps of sensing activity of the heart, monitoring the activity of the heart in accordance with received command transmissions transmitted from a non-implanted transmitter, generating data indicative of the monitored activity, providing a receiver and receiving transmissions from the non-implanted transmitter, and enabling the receiver to receive the command transmissions at intervals in time of controlled duration, separated by intervals in time during which reception does not occur.

The present invention still further provides a method for monitoring activity of a human heart or providing therapy to a human heart of a patient, or both. The method includes the steps of providing a receiver for receiving program transmissions transmitted from external to the skin of the patient, monitoring activity of the heart responsive to the program transmissions, transmitting information including locating signals, and providing a movable unit for transmitting said command transmissions, receiving said information and indicating a received signal strength of said locating signals.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

FIG. 2 (a), (b), (c), (d), (e) is a series of diagrams showing two data transmission protocols which may be utilized in the telemetry system of FIG. 1 and which provides verification of accurate reception of data in accordance with the present invention;

DETAILED DESCRIPTION OF THE PREFERRED EMBODIMENT

Figure 1:
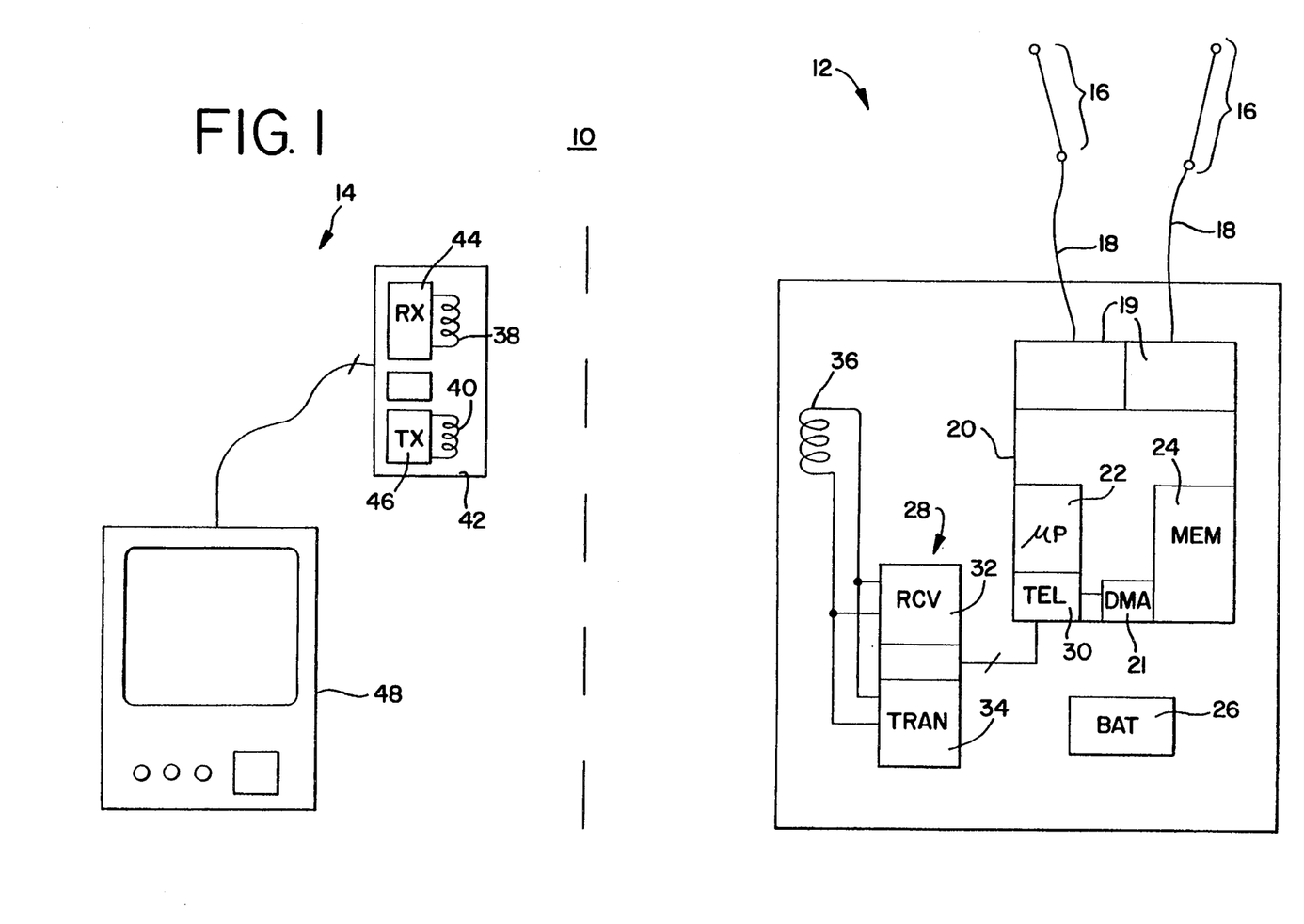
FIG. 1 is a schematic block diagram of a telemetry system for an implantable cardiac device embodying the present invention.

Referring now to FIG. 1, it shows a schematic block diagram of a cardiac system 10 embodying the present invention. The cardiac system 10 generally includes an implantable cardiac device 12 and an external programmer 14.

The cardiac device 12 may be implanted beneath the skin of a patient and includes at least one and preferably a plurality of electrodes 16 carried by leads 18 and adapted to make electrical contact with the heart. The leads 18 are coupled to a circuit means 20.

The circuit means 20 may take the form of a defibrillator, pacemaker or monitor circuit of the type known in the art and capable of monitoring activity of the heart of a patient. When the circuit means 20 takes the form of a defibrillator, it functions to sense heart activity and deliver defibrillating electrical energy to the heart through the electrodes 16 when the heart is in fibrillation. More specifically, the circuit means 20 may take the form of an atrial defibrillator as disclosed, for example, in copending U.S. application Ser. No. 07/685,130, filed Apr. 12, 1991 for Improved Atrial Defibrillator and Method, in the names of John M. Adams and Clifton A. Alferness, which application is assigned to the assignee of the present invention and incorporated herein by reference.

When the circuit means 20 takes the form of a monitor, it detects signals indicative of the functioning of the heart through electrodes 16, converts those signals to digital data and stores the data in memory means 24. More specifically, the circuit means may take the form of a patient monitor as disclosed, for example, in copending U.S. application Ser. No. 07/820,580, filed Jan. 14, 1992 for Implantable Cardiac Patient Monitor, in the names of Barry M. Yomtov and Paul E. Kreyenhagen, which application is assigned to the assignee of the present invention and incorporated herein by reference.

The circuit means 20 includes sensing means 19, a direct memory access ("DMA") controller 21, a microprocessor 22, a memory means 24 and a telemetry support section 30. The sensing means 19 produces digital data corresponding to electrical activity of the heart sensed by the electrodes 16. The memory means 24 stores both command instructions for directing the operation of the microprocessor 22 as well as data indicative of heart activity. The cardiac device also includes a depletable energy source such as a battery 26 which supplies electrical energy to the cardiac device 12.

The cardiac device 12 further includes telemetry means 28. The telemetry means 28 is coupled to the microprocessor 22 through a telemetry support section 30. The telemetry means 28 has a receiving means such as receiver section 32 and a transmitting means such as transmitter section 34. Both the receiver section 32 and the transmitter section 34 are coupled to the antenna 36 for communicating with the external programmer 14.

The external programmer 14 includes a receive coil 38 and a transmit coil 40 in a movable wand or programmer head 42. The programmer head 42 is placed near the chest of the patient in the vicinity of the implanted cardiac device 12 to allow command instructions to be transmitted to the cardiac device 12 and information to be transmitted to the programmer head 42. The programmer head 42 includes external receiving means such as programmer receiver section 44 coupled to the receive coil 38 for decoding information received by the receive coil 38 from the cardiac device 12. The programmer head 42 also includes external transmitting means such as programmer transmitter section 46 for encoding command instructions to be transmitted by the transmit coil 40 to the cardiac device 12.

The programmer head 42 is coupled to a programmer interface 48. The programmer interface 48 allows human interface with the cardiac device 12. The programmer interface 48 may include devices for displaying information indicative of heart activity collected by the implantable cardiac device 12. Programmer interface 48 my also include devices for generating command transmissions to be transmitted to the cardiac device 12. Further, programmer interface 48 may allow coupling to telephonic devices to permit transfer of command transmissions to the cardiac device 12 and information from the cardiac device 12 over, for example, telephone lines or cellular telephone links between the patient's location and equipment located, for example, in a doctor's office or hospital.

In operation, the programmer interface 48 sends a command transmission to the cardiac device 12. The command transmission is in the form of digital data. The data are encoded for transmission by the programmer transmitter section 46 which drives the transmit coil 40. Electromagnetic energy is coupled between the transmit coil 40 and the antenna 36 in the cardiac device.

The receiver section 32 of the telemetry means 28 of the cardiac device 12 senses the energy received by the antenna 36 and decodes the signal to digital data. The digital data form a command instruction which is then conveyed to the telemetry support section 30 and the microprocessor 22. The microprocessor 22 acts on the received command instruction, for example, by programming an atrial defibrillator. The microprocessor 22 analyzes digital data produced by the sensing means 19 and stored in the memory means 24 to detect conditions such as fibrillation of the atria. In response to detecting such a condition, the microprocessor causes defibrillating electrical energy to be applied to the atria of the heart through the leads 18 to defibrillate the atria and return the heart to a normal rhythm.

Further, the received command may direct the microprocessor 22 to transfer information including data from the memory means 24 to the external programmer 14. Alternatively, the received command may implement direct memory access (DMA), bypassing the microprocessor 22 and conveying data from the memory means 24 to the telemetry means 28 under control of DMA controller 21. In either case, the information is transferred to the transmitter section 34 of the telemetry means 28. The transmitter section 34 encodes the data for transmission and drives the antenna 36. Electromagnetic energy is coupled between the antenna 36 and the receive coil 38 of the programmer head.

The DMA channel may also be used in the inbound direction to communicate commands from the programmer 14 to the memory means 24 of the implanted cardiac device 12. In this use, the microprocessor 22 is bypassed and commands transmitted from the programmer 14 are received by the implant receiver section 32 and telemetry support section 30 and then are conveyed via the DMA controller 21 to the memory means 24.

The programmer receiver section 44 senses the energy received by the receive coil 38 and decodes the signal to digital data. The digital data are then conveyed to the programmer interface 48 for display or further processing. The telemetry means 28 thus communicates information from the cardiac device 12 to the external programmer 14 in response to a command transmission communicated from the external programmer 14 to the cardiac device 12.

One particular command transmission employed, in accordance with the present invention, is a command transmission which initiates a communications transaction between the external programmer 14 and the cardiac device 12. This is referred to herein as the initiation command. As used herein, the term "wakeup" is meant to denote the full activation of the telemetry means 28 of the cardiac device 12 in response to an initiation command signal from the external programmer 14.

The initiation command is transmitted by the external programmer 14 to convert the telemetry means 28 of the cardiac device 12 from a partially active state to a fully active state. When the telemetry means 28 is in its quiescent state, the receiver section 32 and transmitter section 34 of the telemetry means 28 are generally de-energized. At spaced apart time intervals or during intervals in time of controlled duration separated by intervals in time during which reception does not occur, the telemetry means 28 enters the partially active state wherein the receiver section 32 is energized to detect energy transmitted by the programmer transmitter section 46. If energy is detected, the receiver section remains energized to look for the transmitted initiation command. If the initiation command is detected, the telemetry means 28 is fully activated and the transmitter section 34 responds by transmitting a response code to the external programmer 14. A communications transaction then begins between the external programmer 14 and the cardiac device 12.

The transmission of command transmissions from the external programmer 14 to the cardiac device 12 is preferably in accordance with a first protocol. The transmission of information from the cardiac device 12 to the external programmer 14 is preferably in accordance with a second protocol. FIG. 2 is a series of diagrams illustrating the first and second transmission protocols which provide for verifying accurate reception of data in accordance with the present invention.

According to the second, or outbound, protocol, data are encoded through phase modulation. As is well known in the art, a carrier signal phase shift may be modulated in accordance with the transmitted data. Preferably, a single bit of data is encoded per cycle of the carrier. Such encoding permits high data transfer rates in accordance with a carrier frequency of 4 Mbits per second. The programmer receiver section 44 in the programmer head 42 detects the phase and phase changes of the carrier signal and reproduces the transmitted information and a clock signal.

According to the present invention, both inbound and outbound transmissions include a packet of data. The packet in turn comprises one or more frames. The frames are used for verifying accurate transmission and receipt of communicated data. Following transmission of a packet, the telemetry link is reversed and a packet is transmitted in the opposite direction. The maximum number of frames in a packet is determined so that transmission time in any one direction is below an upper bound. Very large blocks of data are sent as multiple packets.

Figure 2A:
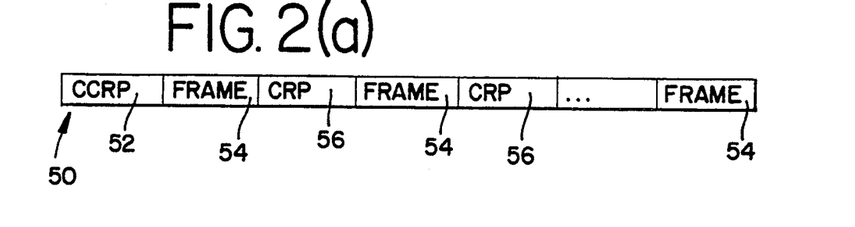

FIG. 2(a) shows an outbound packet 50 of data. The packet includes a carrier and clock recovery pattern ("CCRP") 52 and one or more outbound frames 54 separated by clock recovery patterns ("CRP") 56. The CCRP 52 and the CRP 56 are predetermined patterns of data which allow the programmer receiver section 44 of the programmer head 42 to lock on to the received signal before the programmer receiver section 44 begins receiving frames of data.

Preferably, the length of the outbound frames 54 is fixed. A fixed frame length provides advantages such as simplified error detection and recovery. While a fixed frame length creates the possibility of wasted time and energy for transmission of small blocks of data that do not fill up a frame, this is outweighed by the noted advantages.

Figure 2B:
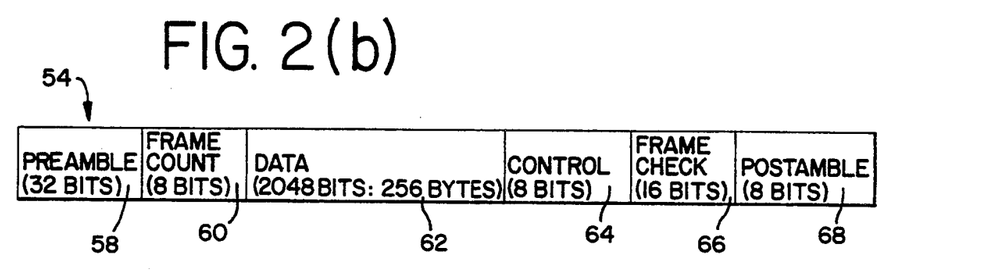

FIG. 2(b) shows an outbound frame 54 of data. The outbound frame 54 includes a preamble 58, a frame count 60, a data field 62, a control byte 64, a frame check 66, and a postamble 68. The preamble 58 is used to determine the start of every outbound frame 54 of an outbound packet following a CCRP 52 or a CRP 56. If the communications channel was free, no further preamble or postamble would be necessary. Since the frames are of fixed length, parsing a frame would require only counting received bits. However, the channel may not be noise free. The preamble 58 and postamble 68 are thus used for error detection and recovery in the event of a noisy channel. For a received frame to be considered error-free, the preamble 58, the postamble 68 and the frame check 66 must match the values expected for each of them by the external programmer 14.

The programmer receiver section 44 in the programmer head 42 counts received bits to determine the position of the fields shown in FIG. 2(b). If bits are missed or inserted due to noise, then the preamble or postamble, which comprise predetermined bit patterns, will be in the wrong place and a framing error will be detected. Following a framing error, the external programmer 14 attempts to recover framing by looking for the next preamble.

The frame count 60 is a sequence number given to each frame. The first frame transmitted has a frame count 60 equal to the total number of frames to be transmitted minus one. The frame count 60 of each subsequent frame is decremented by one. Thus, each transmitted frame has a unique frame count identifier. The external programmer 14 uses the frame count 60 for recovery of outbound transmissions. The final frame sent has a frame count 60 of zero, which value may be used to determine that it is the final frame. The control byte 64, among other functions, may be used to indicate the last frame in the packet 50.

Other portions of the frame contain error-checking information as well. The control byte 64 preferably echoes the command that invoked the outbound transmission. The frame check 66 comprises a block type error detecting code such as cyclic redundancy check code CRC-16, well known in the art.

Lastly, the data field 62 may contain various kinds and amounts of information, depending on the con, hand that invoked the outbound transmission. This information may be the data indicative of monitored heart activity produced by the sensing means 19 and stored in the memory means 24 for transmission to the external programmer 14.

Turning now to command transmissions (inbound transmissions) which are transmitted from the programmer head 42 to the implantable cardiac device 12, such command transmissions are transmitted according to a first, or inbound, protocol. In accordance with the present invention, data to be transmitted from the programmer head 42 pulse width modulates a carrier signal by turning on and off the signal. For example, a logical 1 may be transmitted by turning on the carrier signal for one-third of the bit period. A logical 0 may be transmitted by turning on the carrier signal for two-thirds of the bit period. In this manner, the carrier is amplitude modulated in accordance with the data to be transmitted.

In accordance with the present invention, inbound transmissions occur at two different speeds. During transmissions which initiate a communications transaction between the external programmer 14 and the cardiac device 12, commands are transmitted at a first, relatively low, data rate, such as 2,048 bits per second. Because power consumption is proportional to clock rate, a low data rate during this initiation procedure saves power in the cardiac device 12. However, once the initiation procedure has been completed and a data link has been established between the cardiac device 12 and the external programmer 14, it is preferable to transmit data as quickly as possible so that the receiver section 32 and the transmitter section 34 of the cardiac device 12 are only energized briefly. Accordingly, once the initiation procedure is completed, command transmissions are transmitted at a second, relatively high data rate such as 131,072 bits per second. The ability to transmit and receive at multiple speeds also allows both the external programmer 14 and the cardiac device 12 to be adapted to communicate with other devices. In accordance with the first protocol, then, inbound transmissions are at one of two possible rates.

Figure 2C:
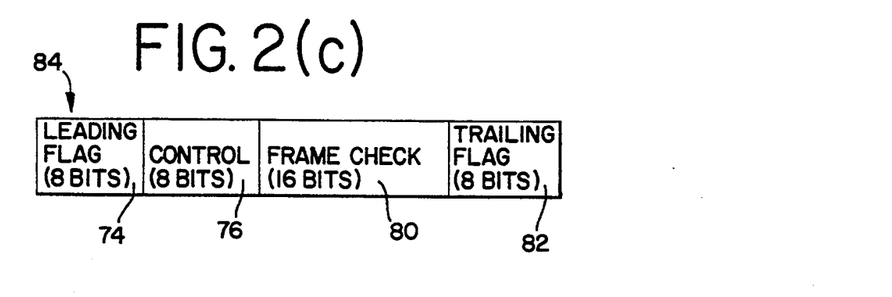

FIG. 2(c) shows a low-speed inbound frame 84 in accordance with the first protocol. A leading flag 74 and a trailing flag 82 aid in delimiting the frame. A control byte 76 contains the command (such as the aforementioned initiation command) being transmitted to the cardiac device 12. The frame check 80 is a block type error detecting code such as CRC-16, well known in the art.

Figure 2D:
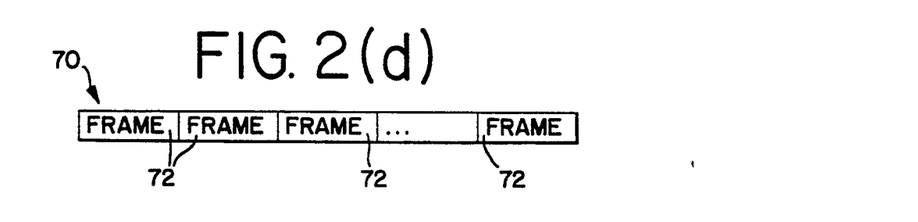
Figure 2E:
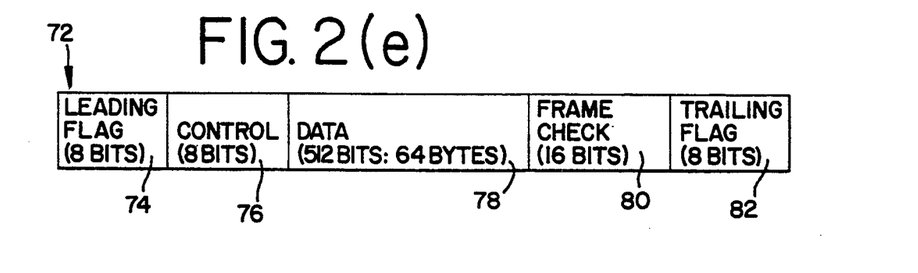

FIG. 2(d) shows an inbound packet 70, in accordance with the first protocol. The inbound packet 70 includes one or more inbound frames 72. FIG. 2(e) shows a high-speed inbound frame 72. The high-speed inbound frame 72 includes a leading flag 74, a control byte 76, a data field 78, a frame check 80 and a trailing flag 82. The data field 78 may contain various kinds and amounts of data depending on the command. The control byte 76, among other functions, is used to indicate the last frame in the packet 70.

Figure 3:
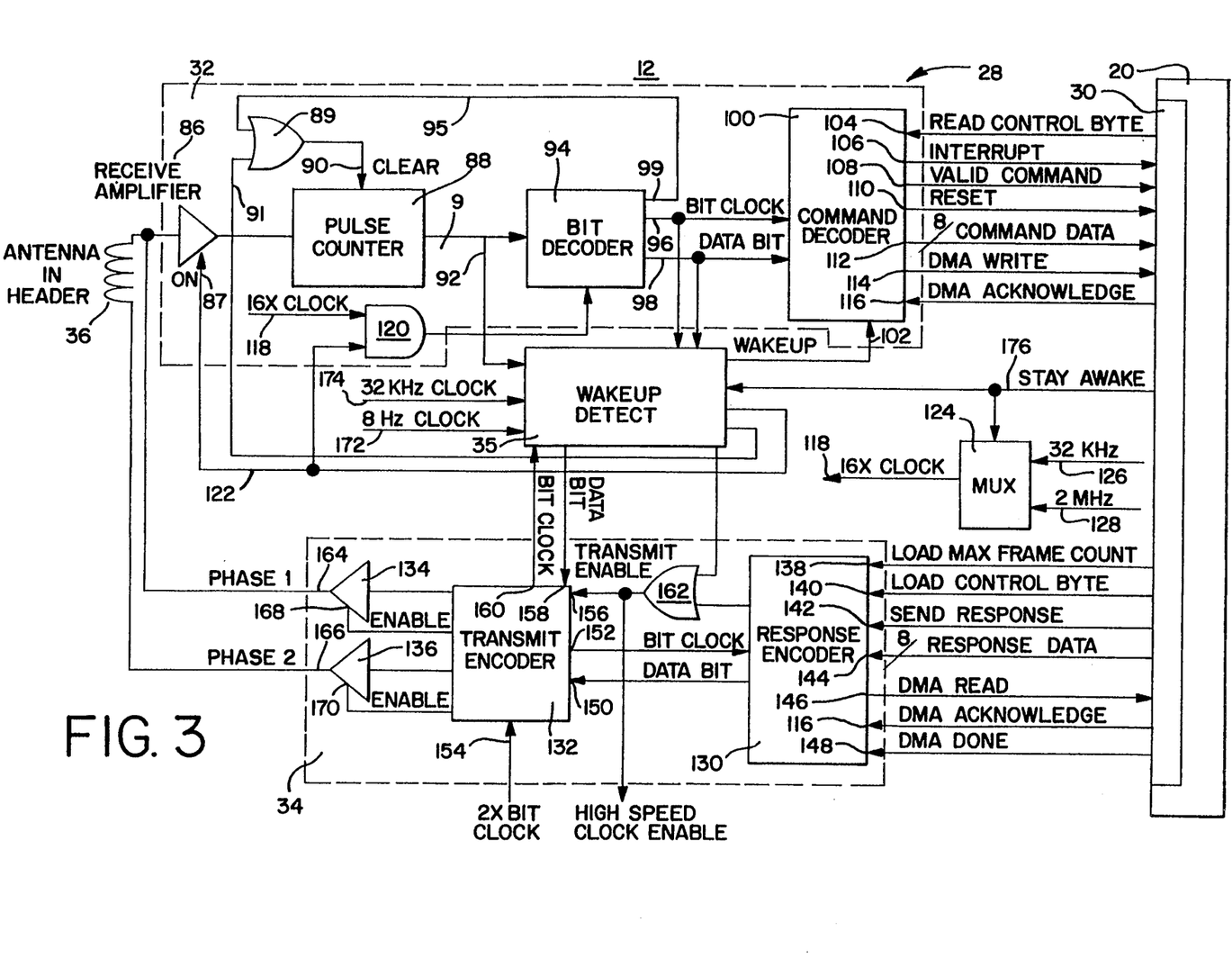
FIG. 3 is a schematic block diagram of an implantable cardiac device embodying the present invention capable of communicating with a non-implanted external receiver and transmitter in accordance with the present invention.

Turning now to FIG. 3, it illustrates in schematic block diagram form an implantable cardiac device 12 embodying the present invention capable of communicating with a non-implanted external receiver and transmitter in accordance with the present invention. Cardiac device 12 includes the telemetry means 28 and the circuit means 20 which includes telemetry support 30. As previously mentioned, the cardiac device 12 is capable of being fully implanted beneath the skin of a patient for monitoring activity of the heart of the patient and/or providing therapy to the heart.

The telemetry means 28 includes the receiver section 32, a transmitter section 34, a wakeup detect 35 and an antenna 36. The receiver section 32 is coupled to the antenna 36. The antenna 36 is preferably located in the neck of the metal enclosure (not shown) which contains cardiac device 12, as disclosed, for example, in the aforementioned U.S. application Ser. No. 07/820,580. By placing antenna 36 outside the metal enclosure, the metal enclosure will not act as a low pass filter to limit the bandwidth of the signals transmitted and received by the antenna 36. Rather, signals may be transmitted and received at high carrier frequencies such as, for example, 8 MHz.

The receiver section 32 includes a receive amplifier 86 coupled to the antenna 36. The receive amplifier 86 has an enable input 87. The receive amplifier 86 is coupled to a pulse counter 88 which has a clear input 90. The pulse counter 88 is coupled by data bus 92 to the bit decoder 94. The bit decoder 94 decodes incoming data bits in response to a pulse count received from the pulse counter 88 over data bus 92. The bit decoder 94 has a bit clock output 96 and a data bit output 98. The bit decoder 94 supplies decoded bits of received data to a command decoder 100 over these two outputs. The bit decoder 94 also has a clear output 99. Clear output 99 is coupled to the clear input 90 of the pulse counter 88 by the clear line 95 and an OR gate 89. The other input of the OR gate 89 is coupled by enable line 91 to wakeup detect 35 which can independently clear the pulse counter 88.

The command decoder 100 has a wakeup input 102. The command decoder 100 is coupled to telemetry support 30 of the circuit means 20 through read control byte input 104, interrupt output 106, valid command output 108, reset output 110, command data bus 112, DMA write output 114, and DMA acknowledge input 116.

In operation, the receive amplifier 86, when enabled at its enable input 87, detects electromagnetic energy received by the antenna 36 and converts that energy into digital pulses for use by the pulse counter 88. In accordance with the first data transmission protocol, the pulse counter 88 counts the number of inbound carrier pulses it receives and produces a pulse count on the data bus 92.

The data bus 92 supplies to the bit decoder 94 the number of pulses counted by the pulse counter 88. The bit decoder 94 preferably samples the 9-bit output data bus 92 at a frequency sixteen times the bit rate.

The bit decoder 94 is responsive to clocking signals on 16X Clock line 118, which is coupled to bit decoder 30 through an AND gate 120. The other input to the gate 120 is coupled to the on or enable line 122. The on line 122 is coupled to wakeup detect 35 and enable input 87 of receive amplifier 86. Signals on line 122 enable both the receive amplifier 87 and gate the clock signal on the 16X clock line 118. The clock signal on 16X Clock line 118 is selected by multiplexer 124 from either the clock signal on 32 KHz clock line 126 or the clock signal on 2 MHz clock line 128 supplied by the telemetry support 30 of the circuit means 20. When a low-speed inbound transmission or the initiation command is expected, the clock signal on the 32 KHz clock line 126 is supplied to the bit decoder 94. When a high-speed inbound transmission is expected, the clock signal on the 2 MHz clock line 128 is supplied to the bit decoder 94. Thus, the bit decoder 94 can accurately decode inbound bits at both data rates according to the first protocol.

The bit decoder 94 uses the number of pulses counted to determine the start of a received bit, the end of a received bit, and the logical value of the received bit. If the number of carrier pulses counted by the pulse counter 88 is greater than a predetermined number, the bit is decoded to be, for example, a logical 0. If the number of carrier pulses counted by the pulse counter is less than the predetermined number, the bit is decoded to be, for example, a logical 1. After decoding a bit, the bit decoder 94 supplies the command decoder 100 a bit clock signal on the bit clock output 96 and the decoded data bit on data bit output 98. The bit counter 88 is cleared every cycle of the 16X clock 118.

The command decoder 100 uses the signals from the bit clock output 96 and the data bit output 98 to determine boundaries of the bytes that form the inbound frames 72 (FIG. 2(d)) based on the leading flag 74 of an inbound frame 72. Once a leading flag 74 is detected and byte boundaries have been detected, the command decoder 100 parses the inbound frame 72 and processes the components of the frame as is appropriate. For example, if a low-speed command is expected and received (FIG. 2(c)), the command decoder 100 stores the control byte 76. In response to a signal received at the read control byte input 104, the stored control byte is transferred to the telemetry support section 30 via the command data bus 112. When a sufficient number of bytes have been received to make up the low speed inbound frame 84, the command decoder 100 transmits an interrupt to the circuit means 20 from the interrupt output 106. If the trailing flag 82 and the frame check 80 were correct, the command decoder 100 also conveys a valid command signal from valid command output 108.

Similarly, if a high-speed inbound command is expected (FIG. 2(e)), the command decoder 100 writes the received control byte 76 and the data field 78 into the memory means 24 (FIG. (1)) via direct memory access controller 21. When the last byte has been received, the command decoder transmits an interrupt to the telemetry support 30 of the circuit means 20 from the interrupt output 106. If the trailing flag 82 and the frame check 80 for each frame 72 was correct, the command decoder 100 also conveys a valid command signal from the valid command line 108. The data field 78 of the command is conveyed to the circuit means 20 over the command data bus 112 and a signal from DMA write output 114 notifies the DMA controller 21 of the circuit means 20 that the data on command data bus 112 is to be written directly to the memory means 24. The circuit means 20 responds by supplying a signal to the DMA acknowledge input 116 of the command decoder 100.

If the command decoder 100 decodes a reset command, a hardware reset signal is placed on the reset output 110. The reset command resets the cardiac device 12 by initializing it to a predetermined state. The reset command is hardware decoded and does not require action by the circuit means 20 of the cardiac device 12. The hardware reset command is included because of the possibility that the cardiac device 12 may become completely inert after final manufacture including welding the enclosure. That is, the cardiac device 12 may generate no output and not respond to telemetry transmissions. The hardware reset command allows the circuit means 20 to be initialized to a predetermined state from external to the enclosure of the implantable cardiac device. Accordingly, for this command to function properly, the telemetry means 28 of the cardiac device 12 must be able to operate independently of the circuit means 20. Thus, reception and execution of the reset command must not be software mediated.

Turning now to the transmitter section 34 of telemetry means 28, the transmitter section 34 includes a response encoder 130, a transmit encoder 132 and tristate buffers 134 and 136. The response encoder 130 encodes response transmissions to be transmitted to the external programmer 14 and is coupled to the telemetry support 30 of the circuit means 20 through load max frame count input 138, load control byte input 140, send response input 142, response data bus 144, DMA read output 146, DMA acknowledge input 116, and DMA done input 148.

The transmit encoder 132 is coupled to the response encoder 130 through the data bit input 150 and the bit clock output 152. The transmit encoder also includes 2X bit clock input 154, transmit enable input 156, a wakeup data bit input 158, and a wakeup bit clock output 160. The wakeup data bit input 158, and the wakeup bit clock output 160 are coupled to the wakeup detect 35. The transmit enable input 156 is coupled to the OR gate 162. The OR gate 162 provides transmit enable signals to the transmit enable input 156 from either the wakeup detect 35 or the response encoder 130. The telemetry support 30 of the circuit means 20 supplies clocking signals to the 2X bit clock input 154 to clock the transmission of data by the transmit encoder 132.

The tristate buffers 134 and 136 are coupled to the transmit encoder 132. Each tristate buffer 134 and 136 has an output 164 and 166, respectively, coupled to respective ends of antenna 36. Each tristate buffer 134 and 136 has an enable input 168 and 170, respectively, coupled to transmit encoder 132. When an enable signal is supplied to enable inputs 168 and 170, the tristate buffers 134 and 136 drive a voltage across the antenna 36 and modulate a carrier signal phase shift in accordance with the response transmission data encoded by the response encoder 130. When an enable signal is not supplied to the enable inputs 168 and 170, the tristate buffer outputs 164 and 166 are placed in a high impedance state as is well known in the art.

In operation, information for transmission and for controlling the transmission of data is conveyed to the response encoder 130 over the 8 bit response data bus 144 from the circuit means 20. When the circuit means 20 places on the response data bus 144 the maximum number of frames to be transmitted, the circuit means also conveys a signal to the Load Max Frame Count input 138. The response encoder 130 uses the maximum number of frames to form the frame count byte 60 (FIG. 2(b)). When the circuit means 20 places on the response data bus 144 the control byte 64 which is to be transmitted, a signal is also conveyed to load control byte input 140. The response encoder 130 uses this byte to form the control byte 64 (FIG. 2(b)). When the response encoder 130 seeks to read one or more bytes of outbound information from memory means 24, it conveys a signal from the DMA read output 146. The DMA controller 21 of the circuit means 20 responds by conveying a signal to the DMA Acknowledge line 116 when the information is available to be read from the memory means 24. The requested bytes of information are then conveyed to the response encoder 130 over the response data bus 144. The response encoder 130 uses these bytes of information to form data field 62 (FIG. 2(b)). When the expected number of bytes of outbound information has been transferred to the response encoder 130, the circuit means conveys a signal to the DMA done input 148. When the circuit means sends a signal to the send response input 142, the transmitter section 34 transmits the information.

The response encoder 130 formats outbound frames for transmission in accordance with the second protocol. When the circuit means 20 directs the response encoder 130 to send a response, the response encoder 130 begins encoding an outbound frame 54 by encoding a preamble 58 and a frame count 60 (FIG. 2(b)). The circuit means 20 conveys the control byte 64 to the response encoder 130 which in turn encodes the control byte and the data 62. The data are read directly from the memory means 24. The response encoder 130 then encodes a frame check 66 and the postamable 68 to complete the encoding of the frame. If the circuit means 20 conveys a signal to the DMA done input 148 before the end of a frame, the response encoder 130 completes the frame with data which has no meaning, such as a string of all digital zeroes. The outbound frame 54 is padded with data in this manner to keep its length fixed in accordance with the second protocol. The response encoder 130 will decrement the frame count 60 between each frame and will continue sending frames until the response encoder receives a signal on DMA done input 148 indicating that all data to be encoded have been encoded.

The bits of the encoded outbound transmission are conveyed serially from the response encoder 130 to the data bit input 150 of the transmit encoder 132. The transmit encoder 132 also receives a clock signal at the 2X bit clock input 154 from the circuit means 20. This clock signal is used by the transmit encoder 132 to produce the bit clock signal on bit clock output 152 and bit clock output 160. The bit clock signal is conveyed from the bit clock output 152 to the response encoder 130 to clock the transmission of data to the data bit input 150. The transmit encoder 132 encodes the data received at data bit input 150 for transmission, in accordance with the present invention, at the rate of one bit per clock period of the bit clock.

The transmit encoder 132 controls the tri-state buffers 134 and 136 to drive the antenna 36 with the phase of a carrier signal modulated according to the encoded data. Preferably, a single bit of data is encoded in each phase of the carrier. If a logical 0 is to be transmitted, a first phase waveform of the carrier signal is transmitted. If a logical 1 is to be transmitted, a second phase waveform is sent, the second phase waveform being 180 degrees out of phase relative to the first phase waveform. This is the form of phase modulation known as absolute phase shift keying, well known in the art. According to this form of phase modulation, the phase sense of the received signal may be inverted, causing a transmitted logical 0 to be received as a logical 1 and a transmitted logical 1 to be received as a logical 0. In order to restore the correct sense of the phase, the programmer receiver section 44 must be able to recognize a pattern in the received signal which indicates whether the signal is being received in normal or inverted phase. The preamble 58 of the outbound frame 54 (FIG. 2(b)) can be used to recognize phase sense. Alternatively, a relative phase shift keying form of phase modulation can be used. Absolute phase shift encoding is preferable to relative phase shift in that fewer components operating at the high data rates are required in the implantable cardiac device. A carrier clock signal is also encoded in the carrier.

An important feature of the present invention is provided by the wakeup detect 35 which forms an activation means. The receiver section 32 and the transmitter section 34 of the telemetry means 28 are generally used only intermittently. After command transmissions are received from the external programmer 14 or after information is transmitted from the cardiac device 12 to the external programmer 14, the receiver section 32 and transmitter section 34 may remain inactive for extended periods of time. Since minimizing power consumption of the implanted cardiac device is important, it is preferable to de-energize the receiving means and transmitting means during such periods of inactivity.

However, when the receiver section 32 is de-energized, the cardiac device 12 is not capable of receiving command transmissions. Therefore, in accordance with the present invention, the receiver section 32 generally remains in a de-energized, quiescent state. At spaced apart time intervals, preferably every 125 milliseconds (8 Hz), the wakeup detect 35 energizes receive amplifier 86 and pulse counter 88, enabling the receiver section 32 to sense inbound energy coupled to the antenna 36. This corresponds to the partially energized state of the telemetry means 28. The wakeup detect 35 is coupled to the receive amplifier 86 at the enable input 87 of the receive amplifier 86. When the wakeup detect 35 supplies an enable signal to the enable input 87, the receive amplifier 86 and pulse counter 88 is enabled to detect a transmission command from the programmer transmitter section 46 located in the external programmer 14 (FIG. 1).

A communications session between the external programmer 14 and the cardiac device 12 begins when the external programmer 14 transmits a transmission command in the form of an initiation code to the cardiac device 12. The external programmer 14 transmits the initiation code for a predetermined period of time. The external programmer 14 then waits to detect a response code transmitted by the cardiac device 12. If no response code is detected by the programmer receiver section 44 in programmer head 42 (FIG. 1), the initiation code is retransmitted until a response code is detected.

The wakeup detect 35 receives clock signals from the circuit means 20 on lines 172 and 174 to energize the receiver section 32 for an activation period. The clock signal on line 172 preferably has a frequency of 8 Hz. In response to each received 8 Hz clock signal, the wakeup detect 35 energizes the receive amplifier 86 by supplying an enable signal to enable input 87 for a period at spaced apart time intervals. This enable signal is also supplied to AND gate 120, enabling the 16X clock signal on line 118 to be conveyed to bit decoder 94. Also, the wakeup detect 35 clears the pulse counter 88 by supplying a signal to clear input 90 through the OR gate 89. In order to minimize energy consumption, the duty cycle of this activation period is kept short. The clock signal on line 174 preferably has a frequency of 32 KHz. The activation period is preferably limited to four periods of this 32 KHz clock.

During the activation period, the wakeup detect 35 looks for an indication on the data bus 92 that energy has been received by the receive amplifier 86 and sensed by the pulse counter 88. If the wakeup detect 35 does not receive an indication that received energy has been detected, the wakeup detect 35 de-energizes the receiver section 32 and the receiver section 32 returns to its quiescent state.

If the wakeup detect 35 receives an indication that energy has been detected by the receive amplifier 86, the wakeup detect 35 continues to supply an enable signal to enable input 87 of the receive amplifier 86 in order to sense the initiation code. The initiation code is preferably a predetermined string of bits.

If the wakeup detect 35 detects an initiation code, the wakeup detect 35 can calculate the time in which a response must be transmitted to the external programmer 14. At that time, the wakeup detect 35 de-energizes the receiver section 32 and supplies an enable signal to the OR gate 162 to energize the transmitter section 34. The transmitter section 34 has heretofore been in a de-energized, quiescent state. Responsive to clock signals from bit clock output 160, the wakeup detect then conveys a response code to the response data bit input 158 of the transmit encoder 132 for transmission to the external programmer 14. In accordance with the present invention, the response code is the same as the initiation code.

The transmitter section 34 transmits the response code for a predetermined time period. The wakeup detect 35 then enables the command decoder 100 by supplying an enable signal to wakeup input 102. The command decoder 100 then looks for an inbound command transmitted at low speed.

Once the external programmer 14 receives the response code, and the signal strength is deemed sufficient, it stops transmitting the initiation code and begins transmitting a low speed command. The low speed command may request the cardiac device 12 to identify itself by model number or serial number. Once the command decoder 100 receives and decodes the low speed command, the telemetry means 28 no longer needs to look for a received initiation code and can assume that all inbound transmissions are commands. The command decoder 100 conveys the received low speed command to the circuit means 20. In response, the circuit means 20 supplies a stay awake signal on line 176. The stay awake signal deactivates the wakeup detect 35. The receiver section 32 remains continuously energized. The stay awake signal also selects the 2 MHz clock signal on line 128 at multiplexer 124 so the bit decoder 94 can decode incoming command transmissions at the high data rate.

Figure 4:
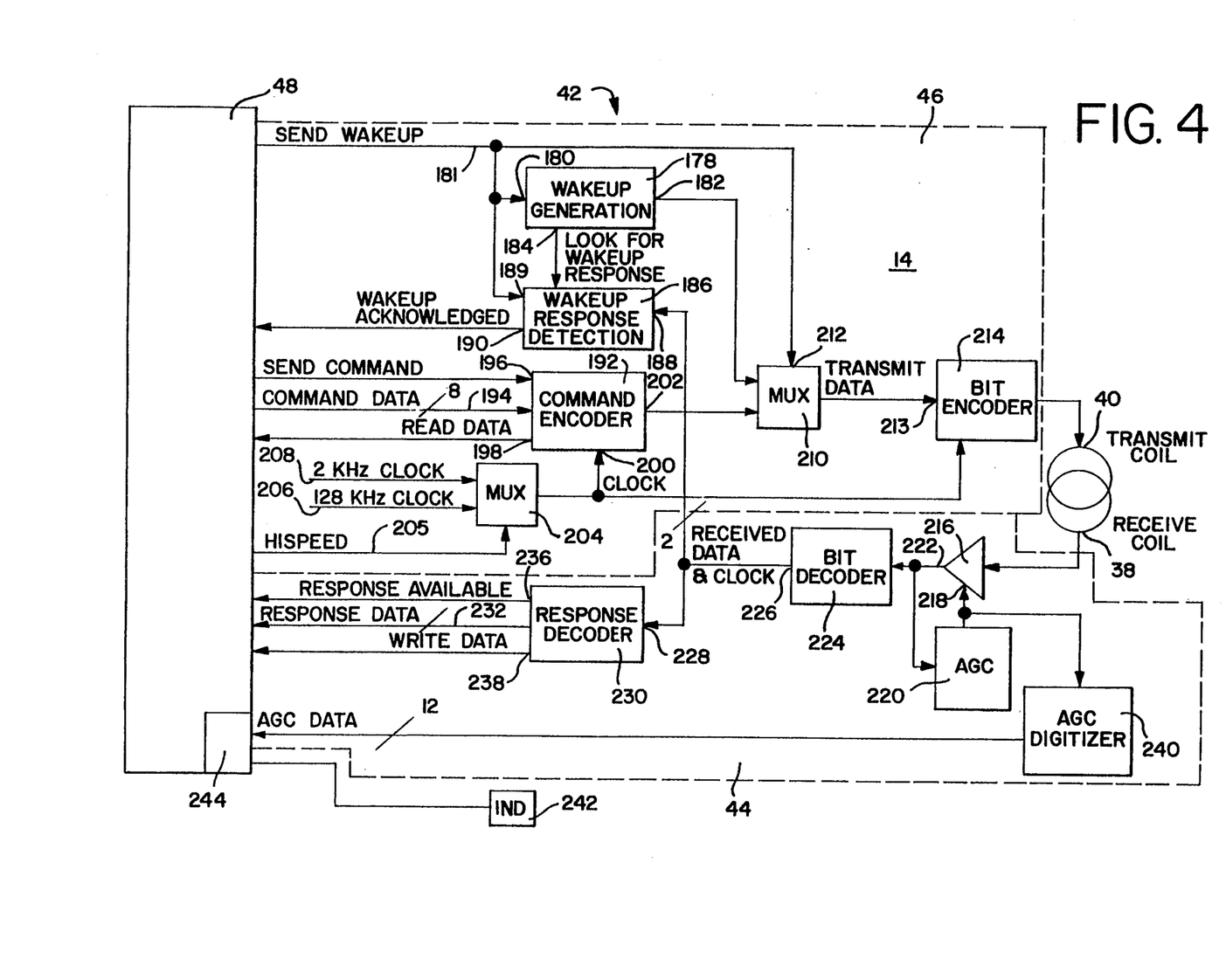
FIG. 4 is a schematic block diagram of an external programmer embodying further aspects of the present invention for communicating with the implantable cardiac device of FIG. 1.

Referring now to FIG. 4, it is a schematic block diagram of an external programmer 14 embodying the present invention for communicating with the cardiac device 12 of FIG. 1. The external programmer 14 generally includes the programmer interface 48 and the programmer telemetry means or programmer head 42. Together, the programmer head 42 and the programmer interface 48 form the external programmer 14 which transmits command transmissions to the cardiac device 12 and receives information from the cardiac device 12.

The programmer head 42, in accordance with the present invention, takes the form of a movable unit or wand which may be positioned externally to the patient in proximity to the cardiac device 12 implanted in the patient. The programmer head 42 includes the receive coil 38 and the transmit coil 40 for coupling electromagnetic energy with the antenna 36 of the cardiac device 12 (FIGS. 1, 2 and 3). Coupled to the receive coil 38 is a programmer receiver section 44 for receiving information from the implantable cardiac device 12. Coupled to the transmit coil 40 is a programmer transmitter section 46 for transmitting program transmissions to the cardiac device 12.

In the programmer transmitter section 46, the wakeup generation 178 is coupled to the programmer interface 48. The wakeup generation 178 has an input 180 coupled to a send wakeup line 181, an output 182 for conveying the wakeup or initiation code and an output 184 coupled to wakeup response detection 186. The wakeup response detection 186 has an input 188, an enable input 189 coupled to send wakeup line 181, and an output 190 coupled to the programmer interface for conveying a wakeup acknowledged signal.

The programmer transmitter section 46 also includes command encoder 192. The command encoder 192 is coupled to the programmer interface 48 by a command data bus 194, a control input 196, a control output 198, and a clock input 200 and has an output 202. The clock input 200 is coupled to a multiplexer 204. Responsive to select signals on select line 205, the multiplexer 204 selects one of two clock signals for clocking the transmission of data, including a high speed clock on line 206, preferably with a frequency of 131,072 Hz, and a low speed clock on line 208, preferably with a frequency of 2,048 Hz. Both clock signals are supplied by programmer interface 48.

The output 182 of the wakeup generation 178 and the output 202 of the command encoder 192 are coupled to a multiplexer 210. The output of the multiplexer 210, responsive to a select signal on the send wakeup line 181 coupled to the select input 212 of the multiplexer 210, conveys serial data received from either output 182 or output 202 to an input 213 of a bit encoder 214. The bit encoder 214 encodes the digital data for driving the transmit coil 40.

In operation, the command encoder 192 receives command transmissions in the form of digital data from the programmer interface 48 and serially shifts the data out at a rate determined by the clock signal at clock input 200. Command transmissions are sent in accordance with a first protocol. The command encoder 192 fashions or assembles the serial stream of bits which form the command transmissions in accordance with the first protocol. If the external programmer 14 is sending a command transmission which is not the initiation code, the multiplexer 210 conveys the output 202 of the command encoder 192 to the bit encoder 214. The bit encoder 214 drives the transmit coil 40 to pulse width modulate a carrier signal in accordance with the digital data received from multiplexer 210 at input 213.

The programmer receiver section 44 includes a programmer receive amplifier 216 coupled to receive coil 38. The programmer receive amplifier 216 has an AGC input 218 coupled to an automatic gain control (AGC) 220. The programmer receive amplifier 216 also has an output 222 coupled to a programmer bit decoder 224 and the automatic gain control 220. The programmer bit decoder 224 has an output 226 coupled to the input 188 of the wakeup response detection 186 and to the input 228 of the response decoder 230. The response decoder 230 is coupled to the response data bus 232 which is also coupled to the programmer interface 48. The response decoder 230 also has two control outputs 236 and 238.

In the operation of the receiver section 44, the programmer receive amplifier 216 detects energy received by the receive coil 38 and amplifies it to voltage levels compatible with the programmer bit decoder 224. The programmer bit decoder 224 receives the amplified received signal and decodes the phase modulation encoded data as well as the carrier clock signal. The decoded data and the decoded clock signal are conveyed to the input 228 of the response decoder 230 and to the input 188 of the wakeup response detection 186.

The response decoder 230 decodes the components of the transmitted information. The response decoder 230 parses the received data to decode the components of an outbound frame 54 (FIG. 2(b)) which are then conveyed to the programmer interface 48. The programmer interface 48 may then use these components for verifying the accuracy of the received information. For example, the programmer interface 48 may determine which, if any, received frames contained errors. As soon as one frame has been received and decoded by the response decoder 230, the response decoder 230 provides a signal at control output 236 to indicate to the programmer interface 48 that a response has been received. The response decoder 230 provides a signal at control output 238 when it writes the response data to the response data bus 232.

The automatic gain control 220 ensures that the level of the amplified received data from the programmer receive amplifier 216 is always within a range which can be interpreted by the programmer bit decoder 224. If the automatic gain control 220 cannot ensure the level, it may be due to the programmer head 42 being moved too far from the cardiac device 12. The automatic gain control 220 responds by providing a signal to the input 218 of programmer receive amplifier 216 which causes the amplification provided by programmer receive amplifier 216 to be varied. An automatic gain control digitizer 240 transforms the analog signal supplied by the automatic gain control 220 to the input 218 into a digital value and supplies the digital value to the programmer interface 48. The programmer interface 48 may use the digital value to determine how far from the implantable cardiac device the programmer head is located.

In accordance with the present invention, the signal strength indicating means 242 provides an indication of received signal strength. The programmer interface 48 may include a signal strength determining means 244. The signal strength determining means 244 uses the digital value provided by the automatic gain control digitizer 240 to determine how far the programmer head 42 is from the cardiac device 12. The signal strength determining means 244 then conveys a signal to the signal strength indicating means 242 which in turn provides an indication. This indication may be visual, such as a light emitting diode array such as bargraph in which the number of illuminated light emitting diodes corresponds to received signal strength, or a flashing LED which flashes at a rate dependent on signal strength, or audible such as a tone with pitch or volume indicative of received signal strength, or a combination of the three. The user, in response to the indication, may then reposition the programmer head 42 to increase the received signal strength. Thus, the signal strength indicating means 242 provides user feedback to allow optimal placement of the programmer head 42 for optimum signal strength from the implanted cardiac device 12.

Figure 5:
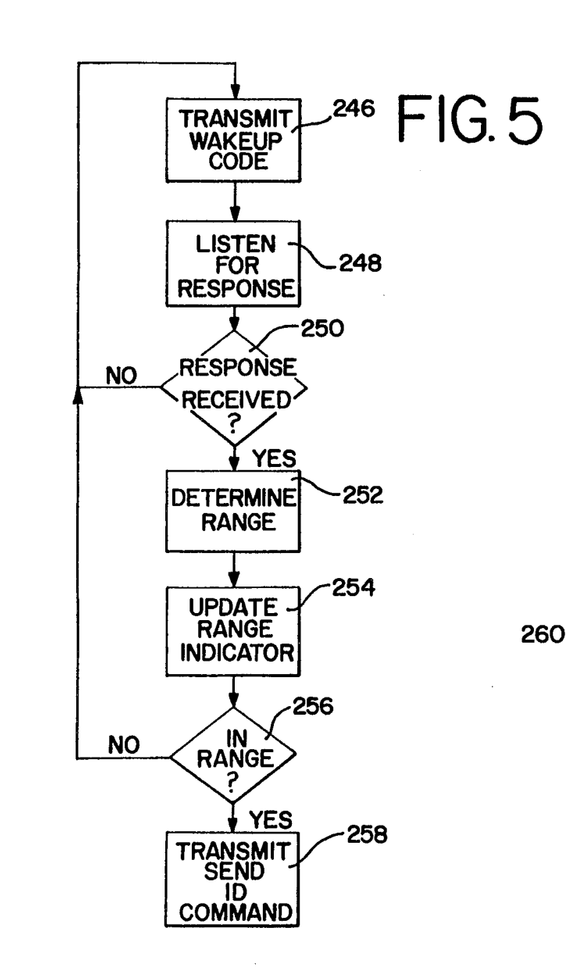
FIG. 5 is a flow diagram illustrating the manner in which the programming unit of FIG. 4 may be implemented in accordance with the present invention for positioning the programming unit for optimal reception of signals from the implantable cardiac device of FIG. 1.

The operation of external programmer 14 to initiate a communications transaction between the external programmer 14 and the cardiac device 12 will now be described in conjunction with FIG. 5. FIG. 5 is a flow diagram illustrating the manner in which the programming unit of FIG. 4 may be implemented in accordance with the present invention for positioning the programming unit for optimal reception of signals from the implantable cardiac device of FIG. 3. This process begins at step 246 with transmission of the initiation code to the implantable cardiac device 12 by the wakeup generation 178 of the programmer head 142. The wakeup generation 178 responds to a send wakeup (initiation) signal received at input 180 from programmer interface 48. In response to receiving the send wakeup signal, the wakeup generation 178 conveys the initiation code to multiplexer 210. In response to the send wakeup signal at the select input 212, the multiplexer 210 conveys the initiation code to the bit encoder 214. The bit encoder 214 drives the transmit coil 40 and pulse wave modulates a carrier signal according to the initiation code.

At step 248, the external programmer 14 listens for a response. During this step, the wakeup detect 35 of the cardiac device 12 energizes the receive amplifier 86 (FIG. 3) to detect the energy transmitted by the programmer head 42. If the initiation code is detected by the cardiac device 12, the cardiac device 12 responds by transmitting information in the form of the response code.

The response code acts as a locating signal for the programmer head 42. At step 250, the external programmer 14 tests if a response code has been received. If the cardiac device 12 transmitted the response code, the programmer receive amplifier 216 may detect the code and the bit decoder 224 will decode the received response code. In response to the send wakeup signal at the input 189 to the wakeup response detection 186, the wakeup response detection 186 will compare the received response with the initiation code. If the response and the initiation codes match, the wakeup response detection 190 will signal the programmer interface 48 by placing a wakeup acknowledged signal on output 190. If no response code has been received, either because the cardiac device 12 did not transmit the response code or because transmission of the response code by the implantable cardiac device is too weak to be detected by the programmer head 42, control is returned to step 246 and the initiation code is re-transmitted.

If the response code is detected, at step 252 the external programmer 14 determines the range from the programmer head 42 to the cardiac device 12 based on received signal strength. During this time, the cardiac device 12, which has detected the initiation code, responds by transmitting the response code to allow the external programmer 14 to lock on to the transmission and determine a received signal strength. There are multiple transmissions of the initiation code by the programmer 14; for every correct reception of the initiation code by the implant 12, the implant transmits the response code. The programmer 14 uses the multiple response codes to effectively lock on to the signal and determine a received signal strength. During step 252, automatic gain control digitizer 240 supplies to the programmer interface 48 a digital value corresponding to the analog signal produced by the automatic gain control 220. The programmer interface 48 uses this digital value to determine the range from the programmer head 42 to the cardiac device 12. At step 254, the programmer interface 48 also uses this digital value to update the light emitting diode bargraph or other signal strength indicating means 242. The user can use this indication to move the programmer head 42 in relation to the implantation site of the cardiac device within the patient in order to properly locate the programmer head 42 for optimal transmission and receipt of telemetry signals.

At step 256, a determination is made whether the programmer head 42 is within range for the programmer receive amplifier 216 in the programmer head 42, under control of the automatic gain control 220, to adequately receive signals from the cardiac device 12. If the programmer head 42 is not within range, control is returned to step 246 and the initiation code is retransmitted. If the programmer head 42 is within range, the initiation or wakeup routine is exited. At step 258 the programmer head 242 stops transmitting the initiation code and in turn transmits, at low speed, an initial command such as a command for the implantable cardiac device to identify itself.

The initial command begins with the preamble 58 of an inbound frame 54. For the implantable cardiac device 12 to clearly distinguish the initial command from the initiation code, the preamble 58 must be clearly distinguishable from the initiation code. Therefore, the initiation code and the preamble preferably are digital bit streams that can't easily be produced from one another. This can be accomplished if the Hamming distance between the bit strings is large and remains large as one bit string is shifted with respect to the other bit string by one or two bits.

Figure 6:
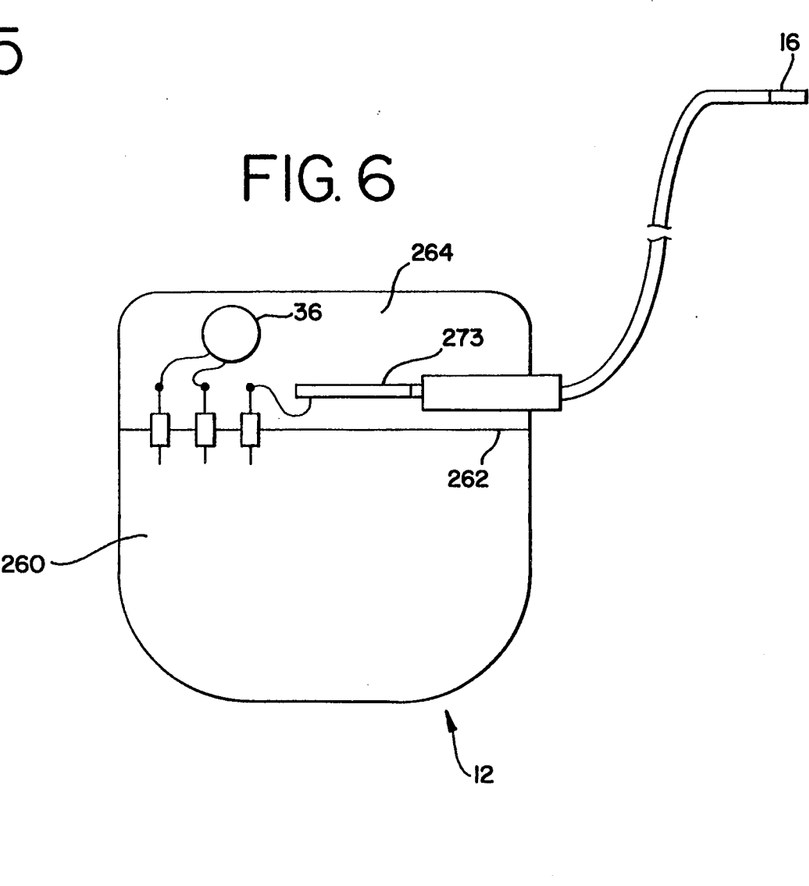
FIG. 6 is a front plan view of an implantable cardiac device illustrating a preferred location for an antenna for efficiently transmitting data characterizing the physiology of the heart from the implantable cardiac device to an external programmer, and for efficiently receiving command transmissions from the external programmer.

Referring now to FIG. 6, it is a front plan view of an implantable cardiac device 12 embodying the present invention. The cardiac device 12 of FIG. 6 includes a hermetically sealed enclosure 260 defining a cavity having a perimeter 262 and a header 264 sealingly engaging the perimeter 262. The cardiac device 12 further includes electrodes 16 for sensing activity of the heart, providing therapy to the heart, or both.

Within the header 264 is the antenna 36. Because the antenna 36 is located within the insulative header 264, efficient telemetry of data will be provided. Also disposed within the header 264 is one or more connectors 273. The connectors 273 may include one or more circuits as needed to connect one or more electrodes 16 as may by required by the cardiac device 12. In accordance with this preferred embodiment, the enclosure 260 may enclose the electrical circuitry previously described.

As can be seen from the foregoing, the present invention provides a new and improved telemetry system comprising the telemetry means 28 of the implantable cardiac device 12 and the programmer telemetry means of the programmer head 42 of the external programmer 14. The improved telemetry system allows reduced power consumption within the implantable cardiac device 12, verification of accurate receipt of data and command transmissions, and accurate location of the external programmer head 42 relative to the implantation site of the implanted cardiac device 12.

While a particular embodiment of the present invention has been shown and described, modifications may be made and it is therefore intended in the appended claims to cover all such changes and modifications which fall within the true spirit and scope of the invention.

What is claimed is:

1. A cardiac device which monitors activity of a human heart, or provides therapy to the human heart, or both, said cardiac device being implantable beneath the skin of a patient and comprising:
   at least one electrode for sensing activity of the heart or providing therapy to the heart;
   circuit means coupled to said at least one electrode for providing therapy or monitoring the activity of the heart sensed by said at least one electrode, said circuit means including data generating means for generating data indicative of said monitored activity or therapeutic activity in accordance with received command transmissions; and
   telemetry means for communicating with a non-implanted external receiver and transmitter, said telemetry means including
   receiving means for receiving said command transmissions from said non-implanted external transmitter, said command transmissions conforming to a first protocol and said command transmissions being selectively transmitted at two or more rates in accordance with said first protocol; and
   transmitting means for transmitting information including said data to said non-implanted external receiver in accordance with a second protocol, said information transmissions being selectively transmitted at one or more rates in accordance with said second protocol,
   said first protocol being different from said second protocol.

2. A cardiac device as defined in claim 1 further including memory means coupled to said circuit means for storing said data and direct memory access means coupled to said memory means and said transmitting means for conveying said data to said transmitting means.

3. A cardiac device as defined in claim 2 wherein said direct memory access means further conveys said command transmissions to said memory means.

4. A cardiac device as defined in claim 1 further including a single antenna coupled to said receiving means and to said transmitting means for both receiving said command transmissions and transmitting said information.

5. A system which monitors activity of a human heart, or provides therapy to the human heart, or both, said system comprising:
   an implantable cardiac device, said implantable cardiac device including at least one electrode for sensing activity of the heart, or providing therapy to the heart, said implantable cardiac device further including circuit means coupled to said at least one electrode for providing therapy or monitoring the activity of the heart sensed by said at least one electrode, said circuit means including data generating means for generating data indicative of said monitored activity or therapeutic activity in accordance with received command transmissions;

a non-implantable external device: and telemetry means for establishing communication between said non-implantable external device and said implantable cardiac device, said telemetry means including a receiver within said non-implantable external device;

a transmitter within said non-implantable external device;

receiving means within said cardiac device for receiving said command transmissions from said transmitter, said command transmissions conforming to a first protocol and said command transmissions being selectively transmitted at two or more rates in accordance with said first protocol; and transmitting means within said cardiac device for transmitting information including said data to said receiver in accordance with a second protocol, said information being selectively transmitted at one or more rates in accordance with said second protocol;

said first protocol being different from said second protocol;

said transmitter including command transmitting means for selectively transmitting said command transmissions at a first rate or at a second rate in accordance with said first protocol.

6. A system as defined in claim 5 wherein said transmitter transmits said command transmissions at said first rate before a communications link is established between said transmitting means and said receiver, and said transmitter transmits said command transmissions at said second rate after said communications link is established.

7. A system as defined in claim 5 wherein, responsive to said first protocol, said transmitter within said non-implantable external device modulates a carrier signal amplitude in accordance with said command transmissions.

8. A system as defined in claim 5 wherein, responsive to said first protocol, said transmitter within said non-implantable external device pulse width modulates a carrier signal in accordance with said command transmissions.

9. A system as defined in claim 5 wherein said receiving means includes verification means for verifying accurate receipt of said command transmissions.

10. A system as defined in claim 9 wherein said telemetry means further comprises a command decoder responsive to said verification means for decoding said command transmissions.

11. A system as defined in claim 9 wherein said command transmissions include one or more inbound frames, said verification means being responsive to said one or more inbound frames for verifying accurate receipt of said command transmissions.

12. A system as defined in claim 11 wherein each inbound frame of said one or more inbound frames includes a leading flag, an inbound frame check, a trailing flag and a control field, said control field including a command for controlling said cardiac device.

13. A system as defined in claim 12 wherein said inbound frame check includes a cyclic redundancy check code.

14. A system as defined in claim 11 wherein said command transmissions are transmitted at a first rate before a communications link is established between said telemetry means and said non-implanted external receiver and said command transmissions are transmitted at a second rate after said communications link is established and wherein each said inbound frame transmitted at said second rate further includes a data field.

15. A system as defined in claim 5 wherein, responsive to said second protocol said transmitting means modulates a carrier signal phase shift in accordance with said data.

16. A system as defined in claim 15 wherein, responsive to said second protocol, said transmitting means modulates said carrier signal using absolute phase shift keying.

17. A system as defined in claim 5 wherein said transmitter within said non-implantable external device includes means for transmitting an initiation command transmission and wherein said telemetry means is responsive to said initiation command transmission for fully energizing said receiving means and said transmitting means of said telemetry means.

18. A system as defined in claim 17 wherein said initiation command transmission comprises a predetermined bit pattern.

19. A system as defined in claim 18 wherein said command transmissions include a preamble, said preamble and said initiation command transmission being different.

20. A system as defined in claim 18 wherein said telemetry means further includes a command decoder and wakeup detect means responsive to said predetermined bit pattern for activating said command decoder to decode said command transmissions.

21. A system as defined in claim 5 wherein said receiver within said non-implantable external device includes verification means for verifying accurate transmission of said information, 22. A system as defined in claim 21 wherein said information includes one or more frames, 23. A system as defined in claim 22 wherein each frame of said one or more frames includes a preamble and a postamble.

24. A system as defined in claim 23 wherein said preamble includes means for determining the beginning of said each frame and a frame count and said postamble includes a control field, a frame check and means for marking the end of said each frame, 25. A system as defined in claim 23 wherein said receiver within said non-implantable external device includes means for uniquely identifying each frame of said one or more frames.

26. A system as defined in claim 5 wherein said telemetry means further includes reset means for initializing said cardiac device to a predetermined state, said reset means operating independently of said circuit means.

27. A system as defined in claim 26 wherein said reset means is responsive to a reset command transmitted from said transmitter within said non-implantable external device for initializing said cardiac device to said predetermined state.

28. A cardiac device which monitors activity of a human heart, or provides therapy to a human heart, or both, said cardiac device being fully implantable beneath the skin of a patient and comprising:
- at least one electrode for sensing activity of the heart or providing therapy to the heart;
- circuit means coupled to said at least one electrode for providing therapy or monitoring activity of the heart sensed by said at least one electrode in accordance with received command transmissions transmitted from a non-implanted transmitter external to the skin of said patient;
- receiving means for receiving said command transmissions from said non-implanted transmitter; and
- activation means for enabling said receiving means to receive said command transmissions at intervals in time of controlled duration separated by intervals in time during which said activation means disables said receiving means from receiving said command transmissions.

29. A system including a cardiac device which monitors activity of a human heart, or provides therapy to a human heart, or both, said cardiac device being fully implantable beneath the skin of a patient, the system comprising;
- a non-implantable transmitter and receiver external to the skin of a patient;
- at least one electrode for sensing activity of the heart or providing therapy to the heart;
- circuit means within said cardiac device coupled to said at least one electrode for providing therapy or monitoring activity of the heart sensed by said at least one electrode in accordance with received command transmissions transmitted from said non-implantable transmitter, said circuit means generating data indicative of monitored activity of the heart;
- receiving means within said cardiac device for receiving said command transmissions from said non-implantable transmitter;
- transmitting means within said cardiac device for transmitting information including said data to said non-implantable receiver responsive to said receiving means receiving an initiation command from said non-implantable transmitter; and
- activation means within said cardiac device for enabling said receiving means to receive said command transmissions at intervals in time of controlled duration separated by intervals in time during which said activation means disables said receiving means from receiving said command transmissions.

30. A system as defined in claim 29 further including a single antenna coupled to said receiving means and to said transmitting means for both receiving said command transmissions and transmitting said information.

31. A system as defined in claim 29 wherein said receiving means includes a receive amplifier, said activation means enabling said receive amplifier to detect said initiation command from said non-implanted transmitter during a predetermined time period during each interval of said intervals in time of controlled duration.

32. A system as defined in claim 31 wherein said activation means enables said transmitting means and said transmitting means transmits a response code to said non-implantable receiver in response to said receive amplifier detecting said initiation command.

33. A system as defined in claim 32 wherein said response code provides confirmation to said non-implanted receiver that said initiation command was received by said cardiac device.

34. A system as defined in claim 32 wherein said receiving means and said transmitting means are de-energized when not enabled.

35. A system as defined in claim 29 further including reset means for initializing said cardiac device to a predetermined state, said reset means operating independently of said circuit means.

36. A system as defined in claim 35 wherein said reset means is responsive to a reset command transmitted from said non-implanted transmitter.

37. A cardiac monitoring or therapeutic system for monitoring activity of a human heart or providing therapy or both, for a patient, said system comprising:
- a cardiac device fully implantable beneath the skin of the patient for monitoring activity of the heart or providing therapy, or both, in accordance with received program command transmissions transmitted from external to the skin of said patient; and
- telemetry means including receiving means within said cardiac device for receiving said program command transmissions, transmitting means within said cardiac device for transmitting information including locating signals, and a movable programming unit including external transmitting means for transmitting said program command transmissions, external receiving means for receiving said information and signal strength indicating means for indicating a received strength of said locating signals.

38. A cardiac system as defined in claim 37 wherein said telemetry means further includes activation means for enabling said receiving means to receive said command transmissions at intervals in time of controlled duration, separated by intervals in time during which reception does not occur.

39. A cardiac system as defined in claim 38 wherein said receiving means and said transmitting means are in a quiescent state until said receiving means receives an initiation command from said external transmitting means.

40. A cardiac system as defined in claim 39 wherein said activation means enables said receiving means to sense said initiation command at said intervals in time of controlled duration and said transmitting means transmits a response code responsive to said receiving means receiving said initiation command.

41. A cardiac system as defined in claim 40 wherein said signal strength indicating means provides an indication of received signal strength responsive to said external receiving means receiving said response code or other command transmissions from said cardiac device.

42. A cardiac device as defined in claim 40 wherein said transmitting means transmits said response code a predetermined time after said receiving means receives said initiation command.

43. A cardiac device for monitoring the physiology of the human heart and delivering therapy to the heart, or both, said device being fully implantable beneath the skin of a patient and comprising:
- a hermetically sealed enclosure, said enclosure including a perimeter, and an electrically insulating header sealingly engaging a portion of said perimeter;
- at least one electrode for sensing activity of the heart;

circuit means within said enclosure and coupled to said at least one electrode for providing therapy or monitoring the activity of the heart sensed by said at least one electrode and for generating data indicative of the monitored activity of the heart responsive to command transmissions received from an external programmer; and one or more antennas disposed within said header for transmitting said data to a non-implanted external receiver and for receiving said command transmissions.

44. A method of communicating in a cardiac monitoring or therapeutic device, said method comprising the steps of:

sensing activity of the heart or providing therapy to the heart;

generating data indicative of said activity in accordance with received command transmissions;

providing a receiver and receiving from a non-implanted transmitter said command transmissions, said command transmissions conforming to a first protocol; and transmitting information including said data to a non-implanted receiver in accordance with a second protocol, said second protocol being different from said first protocol.

45. A method as defined in claim 44 including the further step of establishing a communications link between said non-implanted transmitter and said receiver and transmitting said command transmissions at a first rate before said communications link is established and transmitting said command transmissions at a second rate after said communications link is established.

46. A method as defined in claim 44 wherein said first protocol includes the step of modulating a carrier signal amplitude in accordance with said command transmissions.

47. A method as defined in claim 44 wherein said first protocol includes the step of modulating the pulse width of a carrier signal in accordance with said command transmissions.

48. A method as defined in claim 44 including the further step of verifying accurate receipt of said command transmissions.

49. A method as defined in claim 48 including the further step of decoding said command transmissions.

50. A method as defined in claim 49 wherein said second protocol includes the step of providing said command transmission with one or more inbound frames including a leading flag, an inbound frame check, a trailing flag and a control field, said control field including a command for controlling said cardiac device.

51. A method as defined in claim 44 including the further step of modulating a carrier signal phase shift in accordance with said data.

52. A method as defined in claim 51 wherein said modulating step includes absolute phase shift keying.

53. A method as defined in claim 44 including the further steps of receiving an initiation command transmission and fully energizing said receiver in response to said initiation command transmission.

54. A method as defined in claim 53 wherein said initiation command transmission includes a predetermined bit pattern.

55. A method as defined in claim 53 including the further step of providing a command decoder and wakeup detect means responsive to said predetermined bit pattern for activating said command decoder to decode said command transmissions.

56. A method as defined in claim 44 including the further step of providing a single antenna for both receiving said command transmissions and transmitting said information.

57. A method of communicating in a cardiac monitoring or therapeutic device, said method comprising the steps of:

sensing activity of the heart or providing therapy to the heart;

providing therapy to the heart or monitoring the activity of the heart in accordance with received command transmissions transmitted from a non-implanted transmitter and generating data indicative of said monitored activity;

providing a receiver to receive said command transmissions from said non-implanted transmitter; and enabling said receiver to receive said command transmissions at intervals in time of controlled duration, separated by intervals in time during which said receiver is disabled from receiving said command transmissions.

58. A method as defined in claim 57 including the further step of providing a transmitter to transmit information including said data to a non-implanted receiver.

59. A method as defined in claim 58 including the further steps of detecting an initiation transmission command transmitted from said non-implanted transmitter and enabling said transmitter to transmit a response code to said non-implanted receiver.

60. A method as defined in claim 59 including the further step of de-energizing said transmitter and said receiver when said transmitter and said receiver are not enabled.

61. A method for monitoring activity of a human heart or providing therapy to the heart of a patient comprising the steps of:

providing a receiver for receiving program transmissions transmitted from external to the skin of the patient;

providing therapy or monitoring activity of the heart responsive to said program transmissions;

transmitting information including locating signals; and providing a movable programming unit for transmitting said command transmissions, receiving said information and indicating a received signal strength of said locating signals.

62. A method as defined in claim 61 including the further step of enabling said receiver to receive said command transmissions at intervals in time of controlled duration, separated by intervals in time during which reception does not occur.

63. A method as defined in claim 61 including the further steps of transmitting an initiation command from said movable programming unit to said receiver and transmitting a response code to said movable programming unit.

* * * * *